US00PP33721P2

(12) United States Plant Patent
Thompson

(10) Patent No.: US PP33,721 P2
(45) Date of Patent: Dec. 7, 2021

(54) BLACKBERRY PLANT NAMED 'PBB 1616T'

(50) Latin Name: ***Rubus* L. subgenus *Rubus***
Varietal Denomination: PBB 1616T

(71) Applicant: Pacific Berry Breeding, LLC, Salinas, CA (US)

(72) Inventor: Ellen Thompson, Watsonville, CA (US)

(73) Assignee: Hortifrut North America, Inc., Estero, FL (US)

( * ) Notice: Subject to any disclaimer, the term of this patent is extended or adjusted under 35 U.S.C. 154(b) by 0 days.

(21) Appl. No.: 17/020,213

(22) Filed: Sep. 14, 2020

(51) Int. Cl.
*A01H 5/08* (2018.01)
*A01H 6/74* (2018.01)

(52) U.S. Cl.
USPC ..... Plt./203

(58) Field of Classification Search
USPC ..... Plt./203
CPC ... A01H 5/08; A01H 5/00; A01H 6/74; A01H 6/7499
See application file for complete search history.

(56) References Cited

U.S. PATENT DOCUMENTS

PP28,598 P3 * 11/2017 Clark ..... Plt./203

* cited by examiner

*Primary Examiner* — June Hwu
(74) *Attorney, Agent, or Firm* — King IP Law; Joshua King

(57) ABSTRACT

A new and distinct cultivar of blackberry named 'PBB 1616T' is characterized by early season production of consistently shaped, elongated fruit borne on erect spineless primocanes. This new cultivar is identified, among other things, by its precocity, less intensive cane management needs, firmness, and low color reversion during postharvest performance. Root and subsequent spawn development is moderate in the first year of production.

4 Drawing Sheets

Latin name of the genus and species of the plant claimed: *Rubus* L. subgenus *Rubus*.

Variety denomination: 'PBB 1616T'.

BACKGROUND OF THE INVENTION

Blackberries are a commercially important member of the Rosaceae family, known botanically as *Rubus* L. subgenus *Rubus* Watson. Similar to raspberries (*Rubus idaeus*), individual blackberry fruits are formed by an aggregation of drupelets attached to a fleshy torus (receptacle). Unlike raspberries, the torus remains connected to the blackberry drupelets upon harvest, and is consumed. Each drupelet contains a seed (pyrene), that is surrounded by a fleshy mesocarp (pulp) and exocarp (fruit skin). Blackberries are revered for their health benefits and enjoyed as jams, jellies, juice, frozen and fresh products.

Production of fresh-market blackberries has expanded significantly over the past 20 years, and fruits are now are available globally. Advances in blackberry breeding, in particular the development of primocane-fruiting (remontancy) by the University of Arkansas, has enhanced the ability to produce crops in non-temperate regions, where berries have not been grown historically. Additionally, selection pressure for firmness has allowed for blackberries to be shipped internationally to the high-demand markets of North America and Europe.

Seeds of the present cultivar, 'PBB 1616T', were obtained as part of a bulk seed purchase from a private third party in 2015. No information specific to 'PBB 1616T' was provided from the seller, including that no parental information was disclosed. The identification of 'PBB 1616T' from the germinated plants of the bulk seeds, and subsequent advancement of 'PBB 1616T' was done by the inventor. 'PBB 1616T' offers significant advantages over the existing, patented primocane-fruiting blackberry variety 'APF-45' (marketed under the trade name Prime Ark® 45), U.S. Plant Pat. No. 22,449. Another example of an existing, patented primocane-fruiting blackberry variety is 'APF-122' (U.S. Plant Pat. No. 27,401 P3). A further example of an existing primocane-fruiting blackberry variety is 'APF-190T' (marketed under the trade name Prime Ark® Traveler)', U.S. Plant Pat. No. 28,598 P3.

Compared to 'APF-45', which is spiny, the present cultivar is spineless. Further, the present cultivar requires less intensive cane management, particularly the tipping of canes (removal of the upper 10-15 cm of a vegetative primocane apex), which is critical in the management of 'APF-45'. Intensive cane management leads to higher labor and production costs.

Compared with 'APF-122', berries of the present invention are larger, more elongated and blockier in shape, whereas the former are medium-size and have a conic shape. Under postharvest conditions, 'PBB 1616T' is firmer and develops less color reversion (drupelet reddening) after 7 days in cold storage than 'APF-122'.

Compared to 'APF-190T', the intensity of primocane-fruiting is higher in the present cultivar, allowing a heavier yield in the autumn crop. Plants of 'PBB 1616T' are also more precocious than 'APF-190T', allowing berries to be harvested 5-6 months after planting versus 8-9 months.

Thus, 'PBB 1616T' is a new and distinct primocane-fruiting blackberry cultivar that can be identified, among other things, by its spinelessness, precocity, less intensive cane management needs, firmness, and low color reversion during postharvest performance.

BRIEF DESCRIPTION OF THE PHOTOGRAPHS

DETAILED DESCRIPTION

Figure 1:
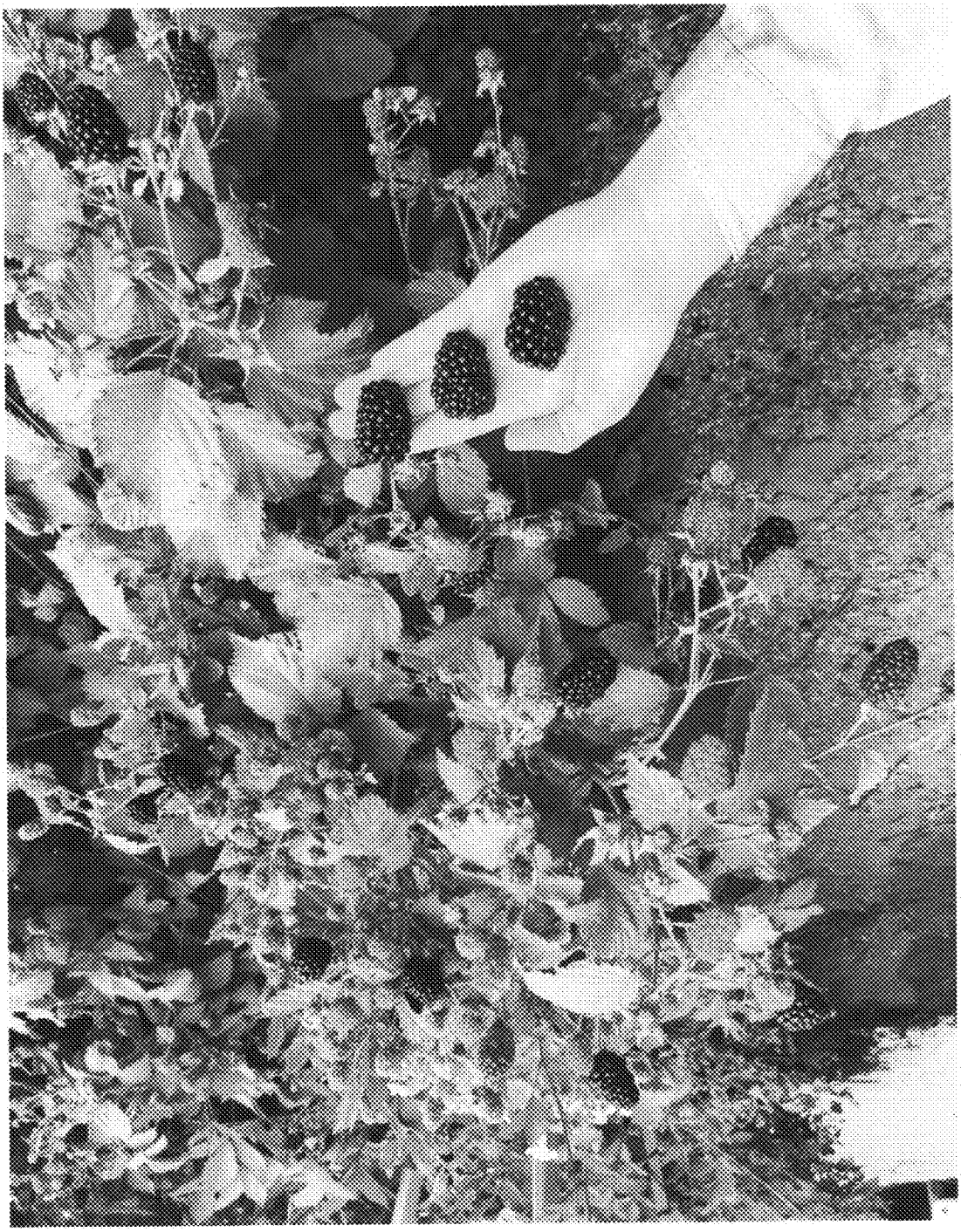
FIG. 1 is a close-up photograph showing the approximate berry size on primocanes and canopy height of 'PBB 1616T'.
Figure 2:
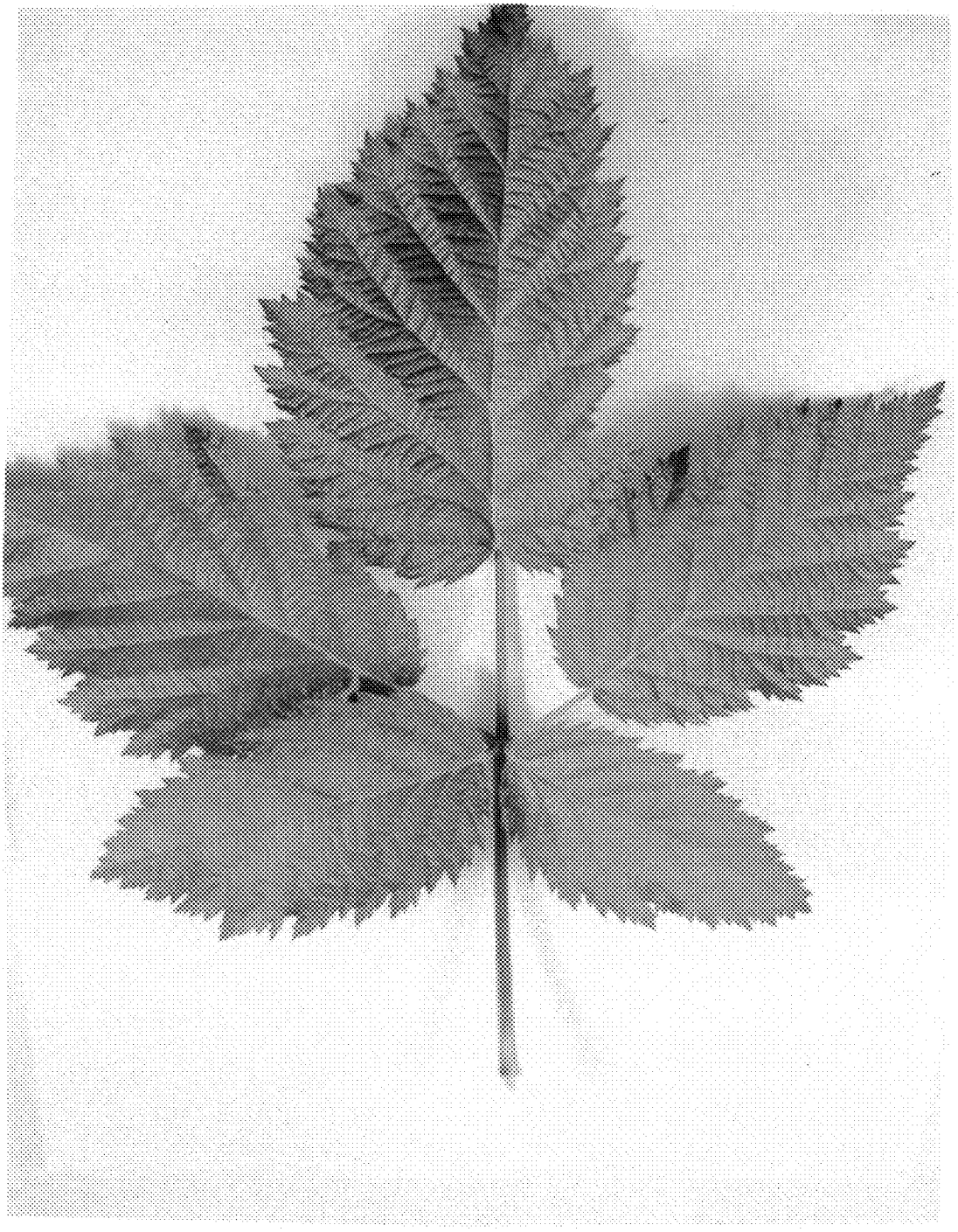
FIG. 2 is a photograph of the pentafoliate leaflet borne from vegetative buds found on 'PBB 1616T'.
Figure 3:
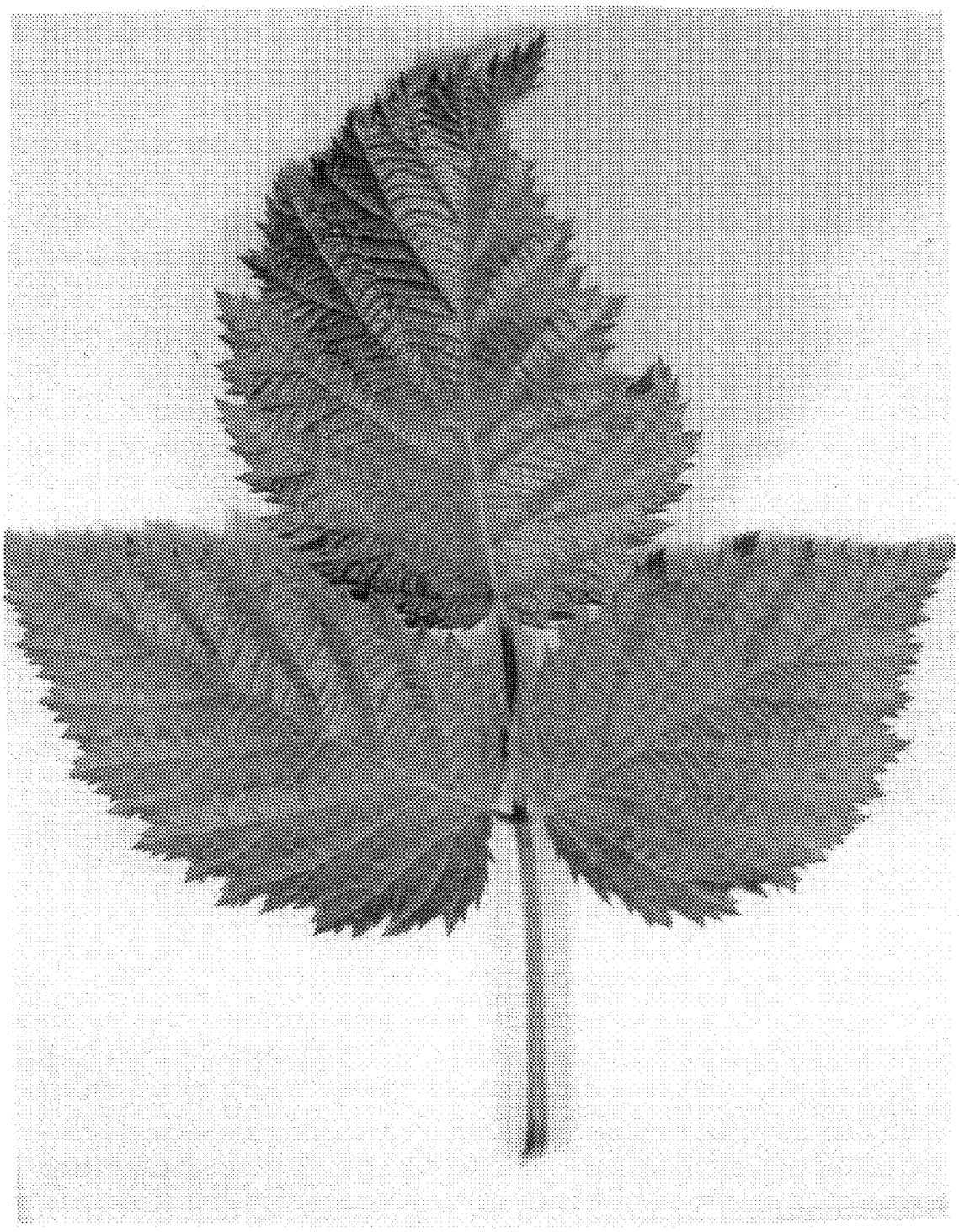
FIG. 3 is a photograph of the trifoliate leaflet borne from reproductive buds found on 'PBB 1616T'.
Figure 4:
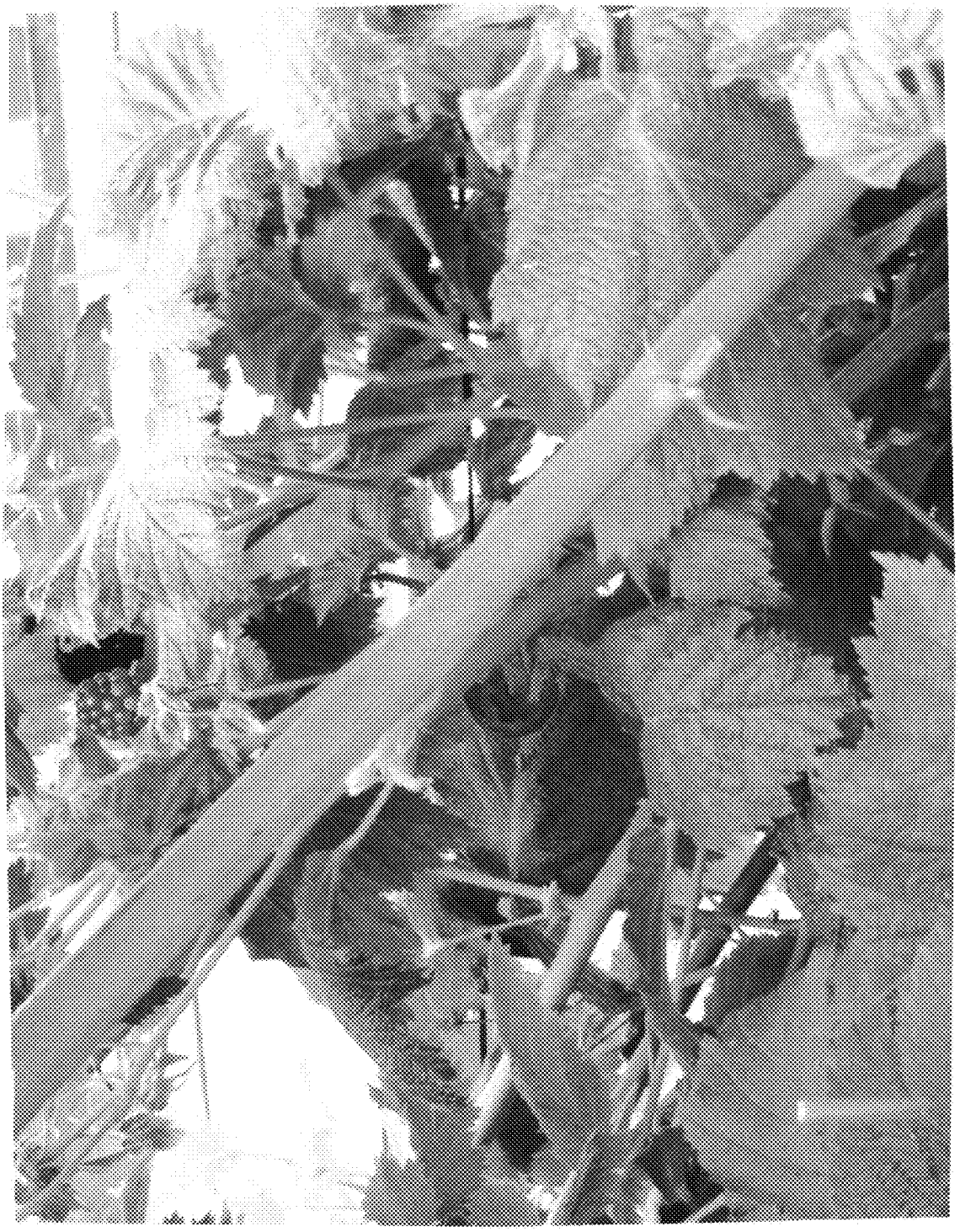
FIG. 4 is a photograph of the spineless cane of 'PBB 1616T'.

Note: statements of characteristics herein represent exemplary observations of the cultivar herein and will vary depending on time of year, location, annual weather, etc. Where dimensions, sizes, colors, and other characteristics are given, it is to be understood that such characteristics are approximations and averages. The descriptions reported herein are from specimen plants at 6 months for primocanes, 14 months for floricanes, with a crown age of 14 months. The specimens were observed in Spring and Autumn 2019 in Watsonville, Calif. The color determination is in accordance with The 2007 R.H.S. Colour Chart (Fifth Edition) of The Royal Horticultural Society, London, England, except where general color terms of ordinary dictionary significance are used.

Cultivar Name: 'PBB 1616T'.

Classification:

Family: Rosaceae.

Botanical name: *Rubus* L. subgenus *Rubus*.

Common name: Blackberry.

Parentage:

Female parent: Unknown.

Male parent: Unknown.

'PBB 1616T' was first identified in a substrate block with other seedlings in September 2016 at Watsonville, Calif. USA. 'PBB 1616T' was first propagated asexually by crown division in November 2016 in Watsonville, Calif. USA. The crown on the original plant was separated into basal cane pieces (approximately 15 cm long) with root attached and replanted into a single larger pot and placed inside a screenhouse on site. The remaining root pieces were chilled for 4 weeks, then planted inside a heated greenhouse to force adventitious shoots. Approximately 20 adventitious shoots were excised, rooted, and planted the following spring for further evaluation of the selection.

In September 2017, two young actively growing primocanes were excised and shipped to Lafayette, Oreg. USA, where vegetative material was explanted and established in vitro for micropropagation. This tissue culture propagation method has allowed for additional, more extensive testing of 'PBB 1616T' and aided in determining that this cultivar is genetically stable.

Growing location for the observations herein: Watsonville, Calif., Santa Cruz County, USA.

Time of year (season): Spring and Autumn 2019.

Age of plants used for this discussion: 6 months for primocanes, 14 months for floricanes.

Age of plants used for the photographs in the Figures: 6 months for primocanes, 14 months for floricanes.

Type of greenhouse covering or growing structure, or field: Substrate block with high tunnel over plants.

Light: Natural.

Pinch dates: May 2019, on young primocanes.

Color terminology where noted were followed using The R.H.S. Colour Chart, Royal Horticultural Society, Fifth Edition, London, United Kingdom (2007).

Observations for floricanes herein were made in May 2019. Observations for primocanes herein were made in September 2019.

Plant:

*Form/shape*.—Vase/Upright.

*Growth habit*.—Erect.

*Height*.—1.9 m as measured from cane base to cane apex.

*Spread*.—72.4 cm as measured from lateral leaf tip to lateral leaf tip.

*Propagation method*.—Tissue culture (in vitro).

*Time to initiate and develop roots*.—25 days.

*Root description*.—Generally of thick diameter, brownish-white color with a smooth, glossy texture. Few feeder roots present. 'PBB 1616T' generally produces spawn (shoots) from roots with moderate vigor.

*Young shoots*.—Anthocyanin coloration during rapid growth: Absent. Intensity of green coloration: Medium. Number of glandular hairs: Medium.

Primocanes:

*Diameter*.—Base: 1.5 cm|Middle: 0.9 cm|Tip: 0.5 cm.

*Length*.—179.3 cm.

*Number of nodes*.—28.

*Internode length*.—Base: 8.8 cm|Middle: 5.1 cm|Tip: 4.6 cm.

*Number of canes/pot*.—11.

*Cane color*.—Undertone is RHS 144A; Overtone is RHS 177A.

*Cane shape in cross-section*.—Rounded Spines (present or absent): Absent. Density: Base — N/A Middle — N/A Tip — N/A. Shape: N/A. Length: N/A. Width: N/A. Apex descriptor: N/A. Color: N/A.

*Bud shape*.—Rounded. Length: 0.64 cm. Diameter (base): 0.19 cm. Diameter (tip): 0.12 cm. Color: RHS 143C. Texture: Mildly pubescent.

Floricanes:

*Diameter*.—Base: 1.2 cm|Middle: 0.9 cm|Tip: 0.9 cm.

*Length*.—89.4 m.

*Number of nodes*.—21.

*Internode length*.—Base: 4.6 cm|Middle: 4.2 cm|Tip: 3.8 cm.

*Cane color*.—

*Lower cane*.—Undertone is RHS 144C; Overtone is RHS 146A.

*Upper cane*.—Undertone is RHS146B; Overtone is RHS 187A.

*Cane shape in cross-section*.—Rounded.

*Spines*.—Absent. Spine density: Base — N/A Middle — N/A Tip — N/A. Spine shape: N/A. Spine length: N/A. Spine width: N/A. Spine apex descriptor: N/A. Spine color: N/A.

*Bud shape*.—Rounded. Length: 0.6 cm. Diameter (base): 0.19 cm. Diameter (tip): 0.12 cm. Color: RHS 143B. Texture: Mildly pubescent.

*Winter hardiness*.—Unknown for 'PBB 1616T' outside of USDA Hardiness Zone 9b (Watsonville, Calif.

USA). This cultivar is well adapted to the mild coastal conditions of California.

*Drought/heat tolerance*.—Pollen viability and fruit quality of blackberry generally begins to decline above 30° C. This is consistent with observations of 'PBB 1616T'. Blackberries are generally drought tolerant, however 'PBB 1616T' has not been tested under unirrigated conditions.

Leaves:

*Time of leaf bud burst*.—Early.

*Complete leaf*.—Type: Palmate. Length: 24.0 cm. Width: 15.8 cm. Number of leaflets: 3 to 5.

*Terminal leaflet*.—Size: Length: 10.5 cm. Width: 10.1 cm. Length/Width ratio: 1.0. Shape of leaf apex: Acute. Shape of leaf base: Terminal leaf: Cordate. Basal lateral leaflets: Cordate. Margin: Triply Senate. Texture: Rigid interveinal puckering. Number of serrations/leaf: 115. Shape of serrations: Flexuous Color: Upper Surface: RHS 147A. Lower Surface: RHS 147B. Venation pattern: Reticulate. Venation Color: Upper surface: RHS 144C. Lower surface: RHS 144D. Leaf pubescence density: Very sparse on topside, only densely present along veins on underside. Color of leaf pubescence: RHS N155A. Shape of leaf in cross-section: Simple cordate leaflet. Number of leaflets/leaf: Primocane: 3 to 5. Floricane: 3 to 5. Interveinal blistering: Present, mild. Glossiness: Absent.

*Primocane leaves*.—Petiole length: 9.0 cm. Petiole diameter: 0.34 cm. Petiole Color: Upper: Undertone is RHS 144C; Overtone is RHS 178A. Lower: Undertone is RHS 146C; Overtone is RHS 144C. Petiole texture: Pubescent. Petiole strength: Very strong. Rachis length: 4.5 cm. Rachis color: RHS177A. Rachis texture: Pubescent. Stipule length: 1.2 cm. Stipules per leaf: 2. Stipule Width: 0.08 cm.

*Stipule color*.—Upper Surface: RHS 144A; On tip RHS 177A. Lower Surface: RHS 146A; On tip RHS 177A.

*Terminal leaflet*.—Length: 10.4 cm. Width: 8.5 cm. Rachis length: 4.8 cm.

*Distal lateral leaflet*.—Length: 10.3 cm. Width: 7.8 cm. Petiolule length: 1.36 cm.

*Basal lateral leaflet*.—Length: 7.7 cm. Width: 5.9 cm. Petiolule length: 0.6 cm.

*Floricane leaves*.—Petiole length: 7.7 cm. Stipule length: 0.9 cm. Stipules per leaf: 2. Stipule Width: 0.1 cm. Stipule Color: RHS 187A. Color: Upper surface: Undertone is RHS 137B; Overtone is RHS 145A; On tip RHS 181A. Lower surface: RHS 137C; On tip RHS 181A.

*Terminal leaflet*.—Length: 9.7 cm. Width: 8.5 cm.

*Distal lateral leaflet*.—Length: N/A. Width: N/A.

*Basal lateral leaflet*.—Length: 8.6 cm. Width: 6.1 cm.

*Petiolule*.—Length: 0.04 cm. Diameter: 0.1 cm. Color: Upper surface: RHS 146C. Lower surface: RHS 146C.

Flowers:

*Time of flowering* (50% *of plants at first flower*).—April 10 on floricanes. June 25 on primocanes.

*Size*.—Length: 1.5 cm. Diameter: 4.3 cm.

*Fragrance*.—Lightly sweet scent.

*Peduncle*.—Length: 6.02 cm. Diameter: 0.19 cm. Color: RHS 144B. Pubescence: Puberulent. Texture: Soft, velvety from puberulence. Strength: Very strong.

*Perianth*.—Flowering trusses shape: Truncate.

*Petals*.—Upper color: Undertone is RHS 157D; Overtone is RHS 65B. Lower color: Undertone is RHS 157D Overtone is RHS N155B. Number per flower: 5. Shape: Obovate. Length: 1.8 cm. Width: 1.6 cm. Apex descriptor: Rounded. Base Descriptor: Truncate. Margin descriptor: Entire. Texture: Smooth with visible striations.

*Sepals*.—Quantity: 5. Length: 1.4 cm. Width: Base: 0.7 cm|Mid: 0.5 cm|Tip: 0.1 cm. Color: Undertone is RHS 145B; Overtone is RHS 138A. Apex descriptor: Acuminate. Outer texture: Pubescent. Inner texture: Puberulent. Margin descriptor: Entire.

*Pedicel*.—Color: RHS 144A. Length: 1.9 cm. Diameter: 0.13 cm. Strength: Very strong.

Reproductive organs:

*Self-fertile*.—Yes.

*Male*.—Stamen number: 140. Filament Length: 0.6 cm. Diameter: 0.01 cm. Color: Undertone is RHS 158D; Overtone is RHS 177C.

*Anther length*.—0.04 cm. Diameter: 0.06 cm. Color: RHS N167A.

*Pollen color*.—RHS 146D. Amount: Sparse.

*Female*.—

*Style*.—Length: 0.2 cm. Diameter: 0.01 cm. Color: RHS 146D.

*Stigma*.—Length: 0.2 cm. Diameter: 0.01 cm. Color: RHS 153A.

*Ovary*.—Length: 0.02 cm. Diameter: 0.004 cm. Color: RHS 145C.

Fruit:

*Fruiting lateral length*.—Medium.

*Predominant shape*.—Blocky.

*Weight*.—6.3 gm.

*Length*.—2.9 cm.

*Width*.—2.0 cm.

*Length/width ratio*.—1.47.

*Receptacle*.—Length: 2.5 cm. Diameter: Base: 0.8 cm|Middle: 0.6 cm|Tip: 0.5 cm. Color: RHS 60A.

*Drupelet*.—Length: 0.6 cm. Diameter: 0.4 cm. Number: 75-90.

*Drupelet weight*.—0.08 gm.

*Fruit color*.—External: RHS 203D. Internal: RHS 203D. Firmness of fruit skin: Very firm. Firmness of fruit flesh: Very firm. Hollow center: Absent (torus present in blackberries). Number of fruit per node: 24 on a fruiting lateral. Time of ripening (50% of plants with first fruit): 25 May on floricanes; 15-August on primocanes. Time of fruiting: Early. Type of bearing: Remontant.

*Fruit yield*.—Floricanes: 6,000 lb/a. Primocanes: 20,000 lb/a. Average brix: 11.3. Acidity: 0.6%. Market use: Fresh. Keeping quality: Excellent. Shipping quality: Excellent.

Pest and disease resistance: Field and substrate trials of 'PBB 1616T' have shown tolerance to *Agrobacterium tumifasciens*, powdery mildew (*Sphaerotheca macularis*), and *Botrytis*. 'PBB 1616T' is susceptible to downy mildew (*Peronospora sparsa*) under cool, wet springtime conditions.

What is claimed is:

1. A new and distinct cultivar of Blackberry plant named 'PBB 1616T' as described and shown herein.

* * * * *